United States Patent [19]

Terasawa et al.

[11] 4,130,565

[45] Dec. 19, 1978

[54] NOVEL TYPE OF OXA- AND THIA-STEROIDS

[75] Inventors: Tadao Terasawa, Ibaraki; Toshihiko Okada, Nara, both of Japan

[73] Assignee: Shionogi & Co., Ltd., Osaka, Japan

[21] Appl. No.: 869,861

[22] Filed: Jan. 16, 1978

Related U.S. Application Data

[62] Division of Ser. No. 739,448, Nov. 5, 1976, Pat. No. 4,083,852.

[51] Int. Cl.$^2$ .................. C07D 309/10; C07D 335/02
[52] U.S. Cl. ........................ 260/327 TH; 260/345.9 S
[58] Field of Search ............... 260/327 TH; 260/345.9

[56] References Cited

U.S. PATENT DOCUMENTS 4,083,852  4/1978  Terasawa et al. ............ 260/327 TH

OTHER PUBLICATIONS

Sih et al., J. Am. Chem. Soc., vol. 87, pp. 1386–1387, (1965).
Grens et al., Chem. Abstracts, abst. No. 58968w, vol. 67, 1967.
Degani et al., Chem. Abstracts, abst. No. 29543u, vol. 68, 1968.

*Primary Examiner*—John D. Randolph
*Attorney, Agent, or Firm*—Wenderoth, Lind & Ponack

[57] ABSTRACT

16-Oxa- and 16-thia-D-homo-estrogen derivatives useful as postcoital oral contraceptives which are produced by total synthesis from 1-vinyltetralin-1-ols or their thiuronium derivatives on reactions with 4-substituted tetrahydropyran- or tetrahydrothiopyran-3,5-diones, and subsequent appropriate modifications.

5 Claims, No Drawings

NOVEL TYPE OF OXA- AND THIA-STEROIDS

This application is a division of application Ser. No. 739,448, filed Nov. 5, 1976, now U.S. Pat. No. 4,083,852 granted Apr. 11, 1978.

The present invention relates to novel type of oxa- and thia-steroids. More particularly, it relates to 16-oxa- and 16-thia-D-homo-1,3,5(10),8,14-estrapentaenes represented by the general formula (I):

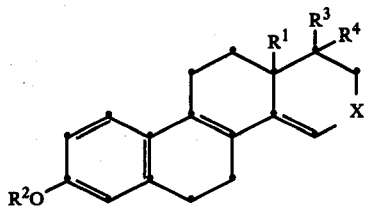

wherein $R^1$ represents a lower alkyl of 1-5 carbon atoms, $R^2$ represents a hydrogen atom or lower alkyl of 1-5 carbon atoms, $R^3$ and $R^4$, one of them represents a hydroxy or acyloxy of 1-5 carbon atoms, and the other represents a hydrogen atom, lower alkyl of 1-5 carbon atoms, ethynyl or aralkyl of 7-8 carbon atoms, or taken together, may represent an oxo group, and X represents an oxygen atom or sulfur atom.

More specifically, said compounds may be represented by the general formulae (Ia), (Ib) and (Ic).

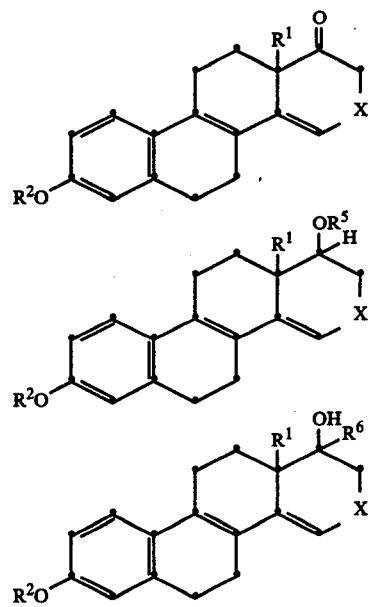

wherein $R^1$, $R^2$ and X each has the same meaning as mentioned above, $R^5$ represents a hydrogen atom or acyl of 1-5 carbon atoms, and $R^6$ represents a lower alkyl of 1-5 carbon atoms, ethynyl or aralkyl of 7-8 carbon atoms.

Large doses of estrogens administered postcoitally to women are known to prevent pregnancy. For example, synthetic estrogens such as ethynylestradiol, mestranol and stilbesterol have been used clinically as postcoital anti-fertility agents. The use of these estrogens, however, is accompanied by some serious adverse reactions attributable to the estrogenicity of the compounds, for example, nausea, vomiting, menorrhagia, altered cycle length, breast soreness, insomnia, etc. It is desirable accordingly to develop new anti-fertility agents in which the anti-fertility action is separated from the estrogenicity.

The present inventors have succeeded in producing a novel type of estrogens having potent anti-implantational activity but less estrogenicity.

In the aforementioned general formulae, the lower alkyl indicated by $R^1$, $R^2$, $R^3$, $R^4$ and $R^6$ includes methyl, ethyl, n-propyl, i-propyl, n-butyl, s-butyl, i-butyl, t-butyl, n-pentyl, 2-methylbutyl, i-pentyl, t-pentyl, and the like. The acyloxy indicated by $R^3$ and $R^4$ includes acetoxy, propionyloxy, butyryloxy, i-butyryloxy, valeryloxy, i-valeryloxy, and the like. The aralkyl indicated by $R^3$, $R^4$ and $R^6$ includes benzyl, phenethyl, and the like. The acyl indicated by $R^5$ includes acetyl, propionyl, butyryl, i-butyryl, valeryl, i-valeryl, and the like.

Representative of the objective compounds (I) are:
3-Hydroxy-16-oxa-D-homo-1,3,5(10),8,14-estrapentaen-17a-one,
3-Hydroxy-16-thia-D-homo-1,3,5(10),8,14-estrapentaen-17a-one,
3-Methoxy-16-oxa-D-homo-1,3,5(10),8,14-estrapentaen-17a-one,
3-Methoxy-16-thia-D-homo-1,3,5(10),8,14-estrapentaen-17a-one,
3-Methoxy-18-methyl-16-oxa-D-homo-1,3,5(10),8,14-estrapentaen-17a-one,
3-Methoxy-18-methyl-16-thia-D-homo-1,3,5(10),8,14-estrapentaen-17a-one,
18-Ethyl-3-methoxy-16-thia-D-homo-1,3,5(10),8,14-estrapentaen-17a-one,
3-Ethoxy-16-thia-D-homo-1,3,5(10),8,14-estrapentaen-17a-one,
3-Methoxy-16-oxa-D-homo-1,3,5(10),8,14-estrapentaen-17aβ-ol,
3-Methoxy-16-thia-D-homo-1,3,5(10),8,14-estrapentaen-17aα-ol,
16-Thia-D-homo-1,3,5(10),8,14-estrapentaene-3,17aα-diol,
3-Methoxy-18-methyl-16-thia-D-homo-1,3,5(10),8,14-estrapentaen-17aα-ol,
3-Methoxy-18-methyl-16-thia-D-homo-1,3,5(10),8,14-estrapentaen-17aβ-ol,
3-Methoxy-18-i-propyl-16-thia-D-homo-1,3,5(10),8,14-estrapentaen-17aα-ol,
18-n-Butyl-3-methoxy-16-thia-D-homo-1,3,5(10),8,14-estrapentaen-17aα-ol,
18-Methyl-3-n-propoxy-16-thia-D-homo-1,3,5(10),8,14-estrapentaen-17aβ-ol,
3-Valeryloxy-16-thia-D-homo-1,3,5(10),8,14-estrapentaen-17aα-ol,
3-Methoxy-17aβ-methyl-16-thia-D-homo-1,3,5(10),8,14-estrapentaen-17aα-ol,
3-Methoxy-17aα-methyl-16-thia-D-homo-1,3,5(10),8,14-estrapentaen-17aβ-ol,
17aβ-Ethyl-3-methoxy-16-oxa-D-homo-1,3,5(10),8,14-estrapentaen-17aα-ol,
3-Methoxy-17aβ-n-pentyl-16-thia-D-homo-1,3,5(10),8,14-estrapentaen-17aα-ol,
17aβ-Benzyl-3-methoxy-16-thia-D-homo-1,3,5(10),8,14-estrapentaen-17aα-ol,
3-Methoxy-17aα-phenethyl-16-thia-D-homo-1,3,5(10),8,14-estrapentaen-17aβ-ol,
17aβ-Benzyl-3-methoxy-18-methyl-16-thia-D-homo-1,3,5(10),8,14-estrapentaen-17aα-ol, 17aβ,18-Dimethyl-3-ethoxy-16-thia-D-homo-1,3,5(10),8,14-estrapentaen-17aα-ol,
17aβ-ethynyl-3-methoxy-16-thia-D-homo-1,3,5(10),8,14-estrapentaen-17aα-ol,
3-Methoxy-17aα-ethynyl-16-thia-D-homo-1,3,5(10),8,14-estrapentaen-17aβ-ol,
17aβ-Ethynyl-3-methoxy-18-methyl-16-oxa-D-homo-1,3,5(10),8,14-estrapentaen-17aα-ol,
17aα-Acetoxy-3-methoxy-16-thia-D-homo-1,3,5(10),8,14-estrapentaene, and
17aβ-Acetoxy-3-methoxy-16-thia-D-homo-1,3,5(10),8,14-estrapentaene.

The objective compounds (I) as mentioned above may be prepared from 1-vinyltetralin-1-ols (IIa) or their thiuronium derivatives (IIb) on reaction with 4-substituted tetrahydropyran- or tetrahydrothiopyran-3,5-diones (III) as illustrated in the following reaction scheme.

under heating. The basic catalysts applicable to this condensation include inorganic bases such as alkali metal hydroxides (e.g. sodium hydroxide, potassium hydroxide) or alkali metal carbonates (e.g. sodium carbonate, potassium carbonate, lithium carbonate); organic bases such as alkali metal acetates (e.g. sodium acetate, potassium acetate), alkali metal alkoxides (e.g. sodium methoxide, potassium methoxide, sodium ethoxide, potassium ethoxide, potassium t-butoxide); quaternary ammonium hydroxides (e.g. Triton B = benzylmethylammonium hydroxide), basic solvents (e.g. pyridine, collidine) or other catalysts (e.g. anion exchange resins, alumina). The organic solvents include alkanols (e.g. methanol, ethanol, isopropanol, n-butanol, t-butanol, isoamyl alcohol), ethers (e.g. ethyl ether, tetrahydrofuran, dioxane, glyme, diglyme), aromatic hydrocarbons (e.g. benzene, toluene, xylene), and the above-mentioned basic solvents as catalysts. The reaction may

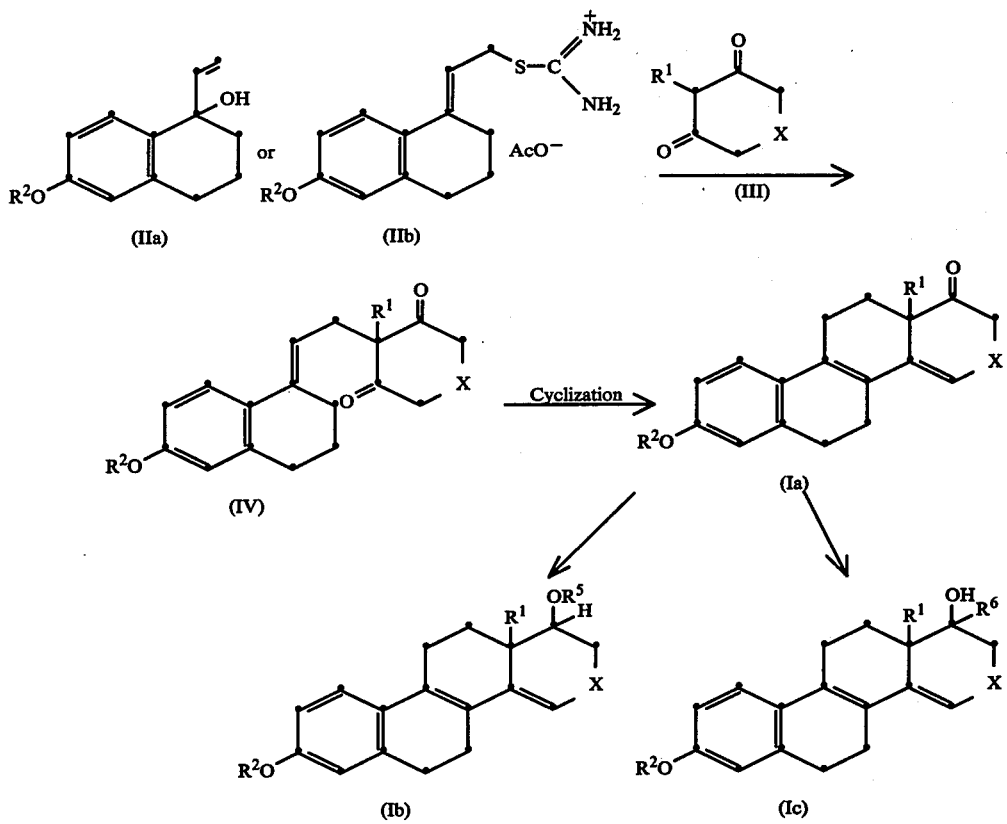

(wherein $R^1$, $R^2$, $R^5$, $R^6$, and X each independently has the same meaning as defined above)

The starting compounds (IIa) and (IIb) used in the invention are known and have been described in, for example, S. N. Ananchenko and I. V. Torgov, Chem. Abstr., 54, 1599 (1960); C. H. Kuo, D. Taub and N. L. Wendler, Angew. Chem., 77, 1142 (1965).

The reaction of the 1-vinyltetralin-1-ols (IIa) or their thiuronium derivatives (IIb) with the tetrahydropyran- or tetrahydrothiopyran-3,5-diones (III) to the tetracyclic compounds (Ia) may be effected substantially according to the method developed by Torgov or its modification in estrogen synthesis [Jean Weill-Raynal, Bull. soc. chim. France, 1969, 4561].

The condensation of the 1-vinyltetralin-1-ols (IIa) with the diones (III) may be carried out in the presence of a basic catalyst, if required in an organic solvent be conducted at approximately 50° C. or higher temperatures, while removing the water produced in the course of the reaction or in the presence of a drying agent such as molecular sieves (Union Carbide, F, MCB, Davison Division of W. R. Grace and Co.), in order to accelerate the reaction.

The condensation of the thiuronium derivatives (IIb) with the diones (III) may be carried out in an aqueous solution at temperatures ranging from room temperature to approximately 60° C. The aqueous solution means water or a mixture of water and an organic solvent, preferably water-miscible organic solvent such as alkanol (e.g. methanol, ethanol, isopropanol), ether (e.g. tetrahydrofuran, dioxane, glyme), dimethylsulfoxide, dimethylformamide, or the like.

The subsequent cyclization of the resulting compounds (IV) to the tetracyclic compounds (Ia) is effected in an organic solvent at an elevated temperature in the presence of an acid catalyst or dehydrating agent. The acid catalysts or dehydrating agents preferably used include organic acids (e.g. formic acid, acetic acid, benzenesulfonic acid, p-toluenesulfonic acid, 2,4-dinitrobenzenesulfonic acid), inorganic acids (e.g. hydrochloric acid, perchloric acid, sulfuric acid, phosphoric acid and/or phosphorous pentoxide), and acid resins. The organic solvents used include lower alkanols (e.g. methanol, ethanol, propanol), halogeno hydrocarbons (e.g. methylene chloride, chloroform, ethylene chloride), aliphatic carboxylic acids (e.g. acetic acid, propionic acid), esters (e.g. ethyl acetate), and aromatic hydrocarbons (e.g. benzene, toluene, xylene). For example, when the reaction is conducted in an aromatic hydrocarbon, the water produced during the reaction can be eliminated as azeotropic mixture from the reaction medium. In such a case, the reaction may preferably be conducted at the refluxing temperature of the solvent used, accordingly.

The conversion of the 17a-oxo compounds (Ia) to the 17a-hydroxy compounds (Ib: $R^5$ = H) may be achieved by reducing agents or appropriate reduction methods applicable to the reduction of carbonyl group. The preferred reducing agents include so-called complex metal hydrides, e.g. lithium aluminium hydride, lithium tri-t-butoxy aluminium hydride, lithium tri-methoxy aluminium hydride, sodium aluminium hydride, sodium borohydride, lithium borohydride, potassium borohydride, zinc borohydride, sodium bis(2-methoxyethoxy)aluminium hydride. The reduction by these reducing agents may be carried out in the conventional manner according to the property of each reducing agent. For example, the reduction by lithium aluminium hydride may be conducted in an ethereal solvent, e.g. ethyl ether, tetrahydrofuran, glyme, at an appropriate temperature such as the refluxing temperature of the solvent used. The reduction by sodium borohydride may be conducted in a proper solvent which may contain water, e.g. methanol, ethanol, i-propanol, tetrahydrofuran, dioxane, glyme, diglyme, at room temperature, if required at an elevated temperature.

The acyl derivatives (Ib: $R^5$ = acyl) of the 17a-hydroxy compounds (Ib: $R^5$ = H) may be produced by acylation with acylating agents such as acyl halides (e.g. acetyl chloride, propionyl chloride, valeryl chloride), acid anhydrides (e.g. acetic anhydride, i-valeryl anhydride), mixed anhydrides (e.g. mixed anhydrides prepared from acetic acid and ethyl chloroformate, from acetic anhydride and formic acid or from acetyl chloride and sodium formate), combinations of aliphatic carboxylic acids (e.g. acetic acid, propionic acid, valeric acid) and acid catalysts (e.g. p-toluenesulfonic acid), and the like in a conventional manner.

The production of the 17a-substituted derivatives (Ic) from the 17a-oxo compounds (Ia) may be effected according to the general procedures for alkylation, ethynylation and aralkylation of carbonyl compounds.

The alkylation and the aralkylation each may be carried out by means of alkylating agents or aralkylating agents such as alkyl- or aralkyl-magnesium halides (so-called Grignard agents; e.g. methylmagnesium bromide, methylmagnesium iodide, ethylmagnesium bromide, n-propylmagnesium chloride, benzylmagnesium bromide, phenethylmagnesium bromide), and other organometallic compounds involving alkali metal compounds (e.g. methyllithium, ethylsodium, i-propyllithium). The reaction is usually carried out in an aprotic solvent, particularly ethereal solvent, e.g. ethyl ether, tetrahydrofuran, glyme, diglyme, in anhydrous condition at a temperature ranging from room temperature to the refluxing temperature of the solvent used. The reaction temperature and time may be fixed according to the reactivity of the reactants.

The ethynylation of the 17a-oxo compounds (Ia) may be carried out in the conventional manner for ethynylation of carbonyl compounds, for example, by ethynylating agents such as acetylene magnesium halides (e.g. ethynylmagnesium bromide, ethynylmagnesium chloride) or alkali metal acetylides (e.g. sodium acetylide, lithium acetylide, potassium acetylide) prepared from acetylene and alkali metals, appropriate bases (e.g. potassium hydroxide, potassium t-butoxide, potassium t-amyloxide) or alkali metal hydrides (e.g. lithium aluminium hydride). The reactions may usually be conducted in liquid ammonia, ethylenediamine, ethylamine, aniline, dimethylacetamide, hexametapol (HMPT), ethereal solvents (e.g. ethyl ether, tetrahydrofuran, dioxane) or aromatic hydrocarbons (e.g. benzene, toluene, xylene), at a variable temperatures, if required under pressure.

The other starting compounds (III) used in the present invention are novel and may be prepared from commercially available compounds as illustrated in the following reaction scheme.

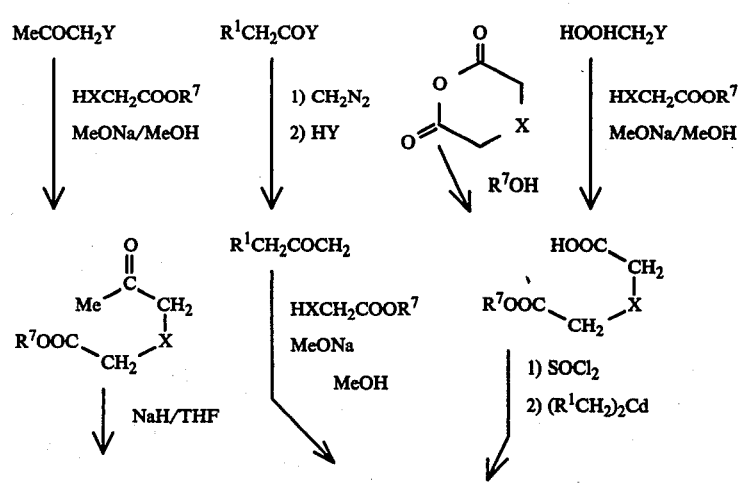

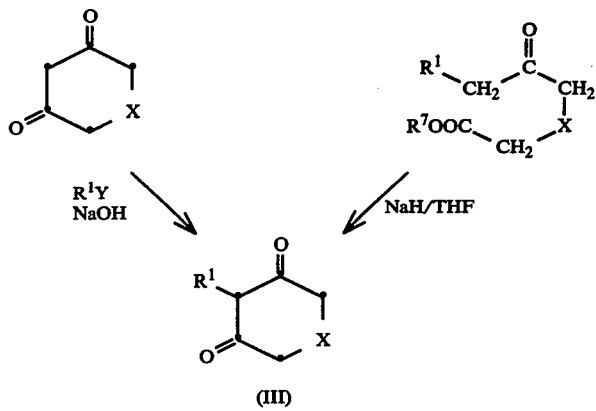

(wherein Y represents a halogen atom, $R^7$ represents an ester residue, and $R^1$ and X each independently has the same meaning as defined above)

The reactions illustrated in the above reaction sequence may be effected in the well-known conventional manners.

The thus resulting objective compounds (I), as mentioned above, have a potent anti-implantational activity and less estrogenicity, and may be used as postcoital contraceptive. The estrogenic activity and anti-implantational activity of the compounds of the present invention were compared with those of a commercially available known estrogen, mestranol. The following table indicates the assay data.

Table

| Compound | Estrogenicity | Anti-implantational Activity | Ratio of AI/D |
|---|---|---|---|
| Mestranol | 100 | 100 | 1.0 |
| A | 12 | 40 | 3.3 |
| B | 12 | 100 | 8.3 |
| C | 22 | 400 | 18 |
| D | 3.7 | 100 | 27 |
| E | 3.6 | 100 | 28 |
| F | 0.84 | 40 | 48 |
| G | 1.3 | 100 | 76 |

Remark:
AI/E = anti-implantational activity/estrogenicity
A = 3-Methoxy-16-thia-D-homo-1,3,5(10),8,14-estrapentaen-17a-one (Ia: $R^1 = R^2 = Me$; X = S)
B = 3-Methoxy-16-thia-D-homo-1,3,5(10),8,14-estrapentaen-17aα-ol (Ib: $R^1 = R^2 = Me$; $OR^3 = α$-OH; X = S)
C = 16-Thia-D-homo-1,3,5(10),8,14-estrapentaene-3,17aα-diol (Ib: $R^1 = Me$; $R^2 = H$; $OR^3 = α$-OH; X = S)
D = 3-Methoxy-18-methyl-16-thia-D-homo-1,3,5(10),8,14-estra-pentaen-17aβ-ol (Ib: $R^1 = Et$; $R^2 = Me$; $OR^3 = β$-OH; X = S)
E = 3-Methoxy-18-methyl-16-thia-D-homo-1,3,5(10),8,14-estra-pentaen-17aα-ol (Ib: $R^1 = Et$; $R^2 = Me$; $OR^3 = α$-OH; X = S)
F = 17aβ-Ethynyl-3-methoxy-16-thia-D-homo-1,3,5(10),8,14-estrapentaen-17aα-ol (Ic : $R^1 = R^2 = Me$; $R^6 = β$-C≡CH; X = S)
G = 3-Methoxy-16-oxa-D-homo-1,3,5(10),8,14-estrapentaen-17aβ-ol (Ib: $R^1 = R^2 = Me$; $OR^3 = β$-OH; X = O)

Test for Estrogenicity (Vaginal TTC Reduction)

Female albino mice of DS colony were used through the experiments. The animals were overiectomized at 29 to 33 days of age under methyl hexabital sodium anesthesia. Ten days after the castration, the test compounds were orally administered through a sonde as a solution dissolved in 0.1 ml of sesame oil. After the lapse of 27 hours, an aqueous solution of 2,3,5-triphenyltetrazolium chloride (TTC) (1 mg/20 μl) was injected into the vaginae, and after 30 minutes the animals were autopsied. The vaginae were isolated, and the formazan formed in the vagina during 30 minutes was quantitatively analyzed by a colorimetric method. The relative potency of the compounds to mestranol was calculated by means of 4-point assay or 6-point assay.

Test for Anti-implantation

Adult female rats of the Wistar strain, weighing 150 g to 200 g, were mated with intact adult male rats. The day on which sperm was found in vagina was designated as Day 1 of pregnancy. A suspension of the test compounds suspended in an aqueous vehicle (consisting of 0.4% polysorvate, 0.5% carboxymethylcellulose, 0.9% benzyl alcohol and 0.9% sodium chloride) was orally administered through a sonde once a day for 6 days, and the animals were laparotomized on Day 8 in order to count the number of implantation sites in both uterine horns. Autopsy was made on Day 15 to count the number of placental sites or scars, fetuses and corpora lutea. The amount of the test compounds administered was increased until no implantation was observed in all animals. The relative potency of the compounds to mestranol was calculated from the minimum amount by which the implantation was inhibited.

In the above table, the respective values of estrogenicity and anti-implantational activity were fixed as relative potency when those of mestranol were regarded as 100.

In addition of these activities, the compounds (I) of the present invention have cholesterol-lowering action, and may also be used as cholesterol lowering agents, accordingly.

When the compounds of the present invention are employed as postcoital oral contraceptives, they may be formulated with suitable excipients in the form of tablets or capsules for oral administration and may be administered within a period of 48 hours after the coition in single or divided doses containing 0.1–4.0 mg a day for more than 4 days.

The invention will be better explained by the following examples which are not intended as a limitation thereof.

In this specification, the numbering of steroidal nucleus and the indication of the α- or β-configuration are designated according to the rules of IUPAC nomenclature system.

EXAMPLE 1

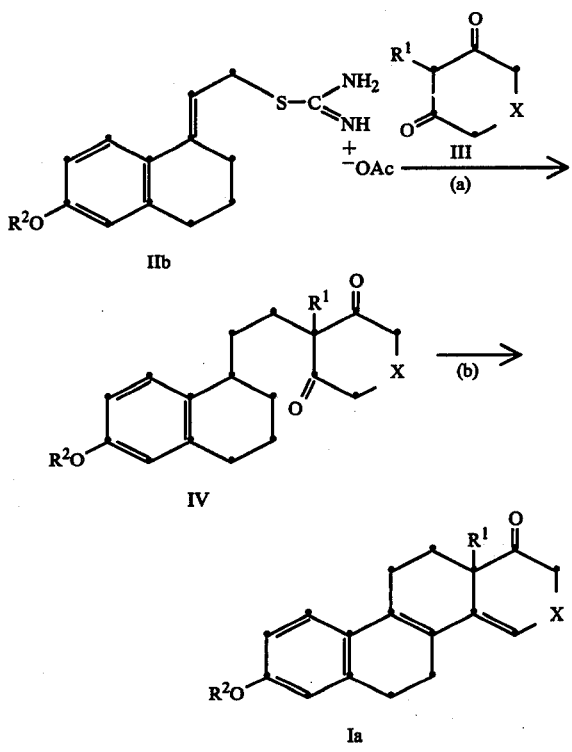

(a)
3-Methoxy-8(14)-seco-16-thia-D-homo-1,3,5(10),9(11)-estratetraene-14,17a-dione (IV: $R^1 = R^2 = Me; X = S$)

To a stirred mixture of 32.2 g (0.1 mole) of the isothiuronium acetate (IIb: $R^2 = Me$) and 14.4 g (0.1 mole) of 4-methyltetrahydrothiopyran-3,5-dione is added 500 ml of 50% aqueous alcohol. A clear solution is observed within 5 minutes followed by precipitation of the product after an additional 5 minutes. The reaction mixture is stirred at room temperature for 3 hours. After standing overnight in a refrigerator, the precipitate is filtered, washed with cold aqueous alcohol and then air-dried to give 28.0 g (84.8% yield) of the dione (IV: $R^1 = R^2 = Me; X = S$), mp. 91.5°–92.5° C. Recrystallization from methylene chloride - ether gives an analytical specimen, mp. 93°–94° C. IR: $\nu_{max}^{Nujol}$ cm$^{-1}$: 1727, 1691, 1604, 1573, 1496. UV: $\lambda_{max}^{EtOH}$ mµ (ε): 267 (18100), 300 (5600; shoulder). NMR: ppm (CDCl$_3$): 1.38 (singlet, 3H, 13-Me), 3.36 and 3.50 (quartet, 4H, J = 14.5, SCH$_2$CO), 3.76 (singlet, 3H, OMe), 5.62 (broad triplet, 1H, J = 7.5, 11-H), 6.60 - 7.49 (multiplet, 3H, aromatic protons). Anal. Calcd. for C$_{19}$H$_{22}$O$_3$S (%): C, 69.06; H, 6.71; S, 9.70. Found (%): C, 68.90; H, 6.66; S, 9.84.

The following compounds can be prepared in the same manner as mentioned above.

3-Methoxy-18-methyl-8(14)-seco-16-thia-D-homo-1,3,5(10), 9(11)-estratetraene-14,17a-dione (IV: $R^1 = Et; R^2 = Me; X = S$): mp. 72°–72.5° C. (recrystallized from ether - pentane). IR: $\nu_{max}^{CHCl_3}$ cm$^{-1}$: 1722, 1693, 1606, 1568, 1493. UV: $\lambda_{max}^{EtOH}$ mµ (ε): 267 (17000), 300 (4900; shoulder). NMR: ppm (CDCl$_3$): 0.83 (triplet, 3H, J = 7.5, 18-Me), 3.78 (singlet, 3H, OMe), 5.66 (broad triplet, 1H, J = 7.5, 11-H), 6.62 - 7.50 (multiplet, 3H, aromatic protons). Anal. Calcd. for C$_{20}$H$_{24}$O$_3$S (%): C, 69.73; H, 7.02; S, 9.31. Found (%): C, 69.55; H, 6.98; S, 9.47.

3-Methoxy-8(14)-seco-16-oxa-D-homo-1,3,5(10),9(11)-estratetraene-14,17a-dione (IV: $R^1 = R^2 = Me; X = O$): mp. 143°-144° C. (recrystallized from methylene chloride - ether). IR: $\nu_{max}^{CHCl_3}$ cm$^{-1}$: 1744, 1714, 1605, 1569, 1497. UV: $\lambda_{max}^{EtOH}$ mµ (ε): 268 (16000), 300 (5100; shoulder). NMR: ppm (CDCl$_3$): 1.36 (singlet, 3H, 13-Me), 3.78 (singlet, 3H, OMe), 4.18 and 4.34 (quartet, 4H, J = 18, OCH$_2$CO), 5.64 (broad triplet, 1H, J = 7.5, 11-H), 6.60 - 7.49 (multiplet, 3H, aromatic protons). Anal. Calcd. for C$_{19}$H$_{22}$O$_4$ (%): C, 72.59; H, 7.05. Found (%): C, 72.38; H, 7.08.

3-Methoxy-18-methyl-8(14)-seco-16-oxo-D-homo-1,3,5(10), 9(11)-estratetraene-14,17a-dione (IV: $R^1 = Et; R^2 = Me; X = O$): mp. 60.5°–61° C. (recrystallized from methanol). IR: $\nu_{max}^{CHCl_3}$ cm$^{-1}$: 1740, 1711 1605, 1567, 1493. UV: $\lambda_{max}^{EtOH}$ mµ (ε): 267.5 (15800), 300 mµ (4600; shoulder). NMR: ppm (CDCl$_3$): 0.83 (triplet, 3H, J = 7.5, 18-Me), 3.77 (singlet, 3H, OMe), 4.19 (singlet, 4H, OCH$_2$CO), 5.62 (broad triplet, 1H, J = 8.0, 11-H), 6.60 - 7.48 (multiplet, 3H, aromatic protons). Anal. Calcd. for C$_{20}$H$_{24}$O$_4$: (%): C, 73.14; H, 7.37. Found (%): C, 72.88; H, 7.40.

(b)
3-Methoxy-16-thia-D-homo-1,3,5(10),8,14-estrapentaen-17a-one (Ia: $R^1 = R^2 = Me; X = S$)

A solution of 6.6 g (20 mmole) of 3-methoxy-8(14)-seco-16-thia-D-homo-1,3,5(10),8,14-estratetraene-14,17a-dione in 100 ml of dry benzene containing 300 mg of p-toluenesulfonic acid monohydrate is heated under refluxing for 10 minutes. The cooled solution is poured into water, and the benzene layer is separated. The aqueous layer is extracted with ether, and the organic layers are combined, washed with an aqueous sodium bicarbonate solution and an aqueous sodium chloride solution, and dried over anhydrous sodium sulfate. The solvent is evaporated in vacuo to give a gummy residue, which is adsorbed on 30 g of neutral alumina and elutated with benzene. The eluates are collected, the solvent evaporated, and the residue is crystallized from methylene chloride - ether to give 5.78 g (92.7% yield) of the objective tetracyclic pentaene (Ia: $R^1 = R^2 = Me; X = S$), mp. 94°–96° C. Recrystallization from the same solvents affords an analytical specimen, mp. 95°–96° C. IR: $\nu_{max}^{CHCl_3}$ cm$^{-1}$: 1705, 1608, 1563, 1496. UV: $\lambda_{max}^{EtOH}$ mµ (ε): 320 (27500; shoulder), 333 (33000), 345 (25500; shoulder). NMR: ppm (CDCl$_3$): 1.37 (singlet, 3H, 13-Me), 3.37 and 3.51 (quartet, 2H, J = 14.0, SCH$_2$CO), 3.80 (singlet, 3H, OMe), 6.37 (broad singlet, 1H, 15-H), 6.69 - 7.32 (multiplet, 3H, aromatic protons). Anal. Calcd. for C$_{19}$H$_{20}$O$_2$S (%): C, 73.04; H, 6.45; S, 10.26. Found (%): C, 73.29; H, 6.51; S, 10.58.

The following compounds can be prepared in the same manner as mentioned above.

3-Methoxy-18-methyl-16-thia-D-homo-1,3,5(10),8,14-estrapentaen-17a-one (Ia: $R^1 = Et; R^2 = Me; X = S$): mp. 105.5°–106.5° C. (recrystallized from ether). IR $\nu_{max}^{CHCl_3}$ cm$^{-1}$: 1703, 1608, 1561, 1493. UV: $\lambda_{max}^{EtOH}$ mµ (ε): 320 (25000; shoulder), 332 (29900), 345 (23500; shoulder). NMR: ppm (CDCl$_3$): 0.80 (triplet, 3H, J = 7.5, 18-Me), 3.40 (singlet, 2H, SCH$_2$CO), 3.79 (singlet, 3H, OMe), 6.38 (broad singlet, 1H, 15-H), 6.64 - 7.28 (multiplet, 3H, aromatic protons). Anal. Calcd. for C$_{20}$H$_{22}$O$_2$S (%): C, 73.58; H, 6.79; S, 9.82. Found (%): C, 73.37; H, 6.71; S, 10.01.

3-Methoxy-16-oxa-D-homo-1,3,5(10),8,14-estrapentaen-17a-one (Ia: $R^1 = R^2 = Me; X = O$): mp. 113°–115° C. (recrystallized from methylene chloride - ether). IR: $\nu_{max}^{CHCl_3}$ cm$^{-1}$: 1721, 1618, 1604, 1563, 1495. UV: $\lambda_{max}^{EtOH}$ mμ (ε): 301 (23500; shoulder), 313.5 (28200), 327 (20100; shoulder). NMR: ppm (CDCl$_3$): 1.28 (singlet, 3H, 13-Me), 3.80 (singlet, 3H, OMe), 4.20 and 4.61 (quartet, 2H, J = 18, OCH$_2$CO), 6.83 (singlet, 1H, 15-H), 6.68 - 7.29 (multiplet, 3H, aromatic protons). Anal. Calcd. for C$_{19}$H$_{20}$O$_3$ (%): C, 77.00; H, 6.80. Found (%): C, 76.73; H, 6.69.

3-Methoxy-18-methyl-16-oxa-D-homo-1,3,5(10),8,14-estrapentaen-17a-one (Ia: $R^1 = Et; R^2 = Me; X = O$): mp. 63°–64.5° C. (recrystallized from ether - pentane). IR: $\nu_{max}^{CHCl_3}$ cm$^{-1}$: 1715, 1617, 1604, 1563, 1494. UV: $\nu_{max}^{EtOH}$ mμ (ε): 301 (23400; shoulder), 313.5 (28200), 327 (19500; shoulder). NMR: ppm (CDCl$_3$): 0.84 (triplet, 3H, J = 7.5, 18-Me), 3.79 (singlet, 3H, OMe), 4.19 and 4.46 (quartet, 2H, J = 18, OCH$_2$CO), 6.88 (singlet, 1H, 15-H), 6.68 - 7.26 (multiplet, 3H, aromatic protons). Anal. Calcd. for C$_{20}$H$_{22}$O$_3$ (%): C, 77.39; H, 7.14. Found (%): C, 77.07; H, 7.12.

EXAMPLE 2

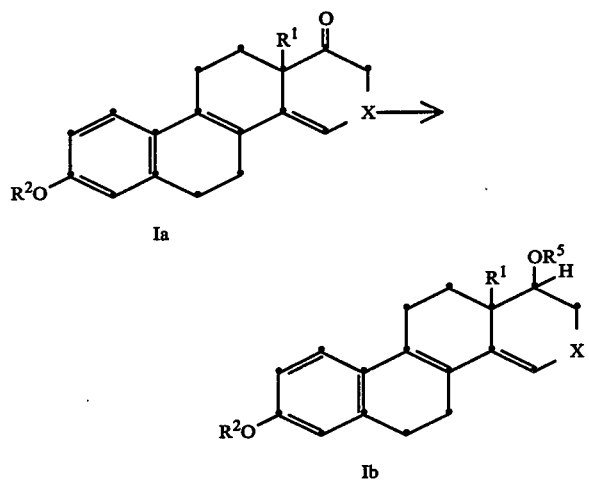

3-Methoxy-16-thia-D-homo-1,3,5(10),8,14-estrapentaen-17a-ols (Ib: $R^1 = R^2 = Me; R^5 = H; X = S$)

Sodium borohydride (115 mg; 3.04 mmole) is added portionwise to an ice-cold stirred suspension of 312.4 mg (1 mmole) of 3-methoxy-16-thia-D-homo-1,3,5(10),8,14-estrapentaen-17a-one in 10 ml of methanol. The suspension turns into a clear solution in a few minutes and then another suspension after 20 minutes. The suspension is stirred at room temperature for 2 hours. The pH is adjusted to 7 with about 0.2 ml of concentrated hydrochloric acid under cooling, and ice-cold water is added thereto. The reaction mixture is extracted with methylene chloride, and the extract is washed with an aqueous sodium chloride solution and dried over anhydrous sodium sulfate. Removal of the solvent leaves a viscous syrup (323 mg), which is purified by preparative thin layer chromatography using silica gel and benzene - ethyl acetate (9:1). The upper band gives 212 mg (67.4% yield) of the 17aα-ol, which is crystallized from methylene chloride - ether to give 198.7 mg (63.2% yield) of crystals, mp. 140°–143° C. Recrystallization from methylene chloride - acetone gives the analytical specimen, mp. 140°–142° C. IR: $\nu_{max}^{CCl_4}$ cm$^{-1}$: 3553. UV: $\lambda_{max}^{EtOH}$ mμ (ε): 318 (30800; shoulder), 329.5 (40400), 345 (30800). NMR: ppm (CDCl$_3$): 0.99 (singlet, 3H, 13-Me), 3.78 (singlet, 3H, OMe), 6.13 (broad singlet, 1H, 15-H), 6.66 - 7.30 (multiplet, 3H, aromatic protons). Anal. Calcd. for C$_{19}$H$_{22}$O$_2$S (%): C, 72.57; H, 7.05; S, 10.20. Found (%): C, 72.39; H, 7.04; S, 10.22.

On the other hand, the lower band gives 87.8 mg (27.9% yield) of the 17aβ-ol, which is crystallized from ether - petroleum ether to give 86.1 mg (27.4%) of crystals, mp. 139°–141° C. Recrystallization from acetone - ether gives the analytical specimen, mp. 140°–141° C. IR: $\nu_{max}^{CCl_4}$ cm$^{-1}$: 3632. UV: $\lambda_{max}^{EtOH}$ mμ (ε): 317 (30400; shoulder), 329 (39700), 343.5 (30400). NMR: ppm (CDCl$_3$): 1.02 (singlet, 3H, 13-Me), 3.78 (singlet, 3H, OMe), 6.02 (broad singlet, 1H, 15-H), 6.65 - 7.29 (multiplet, 3H, aromatic protons). Anal. Calcd. for C$_{19}$H$_{22}$O$_2$S (%): C, 72.57; H, 7.05; S, 10.20. Found (%): C, 72.21; H, 7.03; S, 10.24.

The product ratio of the 17aα-ol to the 17aβ-ol is 2.4 to 1.0.

The corresponding acetates (Ib: $R^1 = R^2 = Me; R^5 = Ac; X = S$) are prepared by acetylation using acetate anhydride and pyridine.

17aα-Acetate: mp. 136°–137° C. (crystallized from ether - petroleum ether). IR: $\nu_{max}^{CHCl_3}$ cm$^{-1}$: 1728, 1608, 1560, 1486, 1254. UV: $\nu_{max}^{EtOH}$ mμ (ε): 315 (31400, shoulder), 328.5 (41500), 343.5 (31300). NMR: ppm (CDCl$_3$): 1.07 (singlet, 3H, 13-Me), 2.10 (singlet, 3H, OCOMe), 3.80 (singlet, 3H, OMe), 4.98 (triplet, 1H, J = 3, 17aβ-H), 6.21 (broad singlet, 1H, 15-H), 6.68 - 7.31 (multiplet, 3H, aromatic protons). Anal. Calcd. for C$_{21}$H$_{24}$O$_3$S (%): C, 70.75; H, 6.79; S, 9.00. Found (%): C, 70.92; H, 6.88; S, 9.03.

17aβ-Acetate: mp. 162.5°–164° C. (crystallized from methylene chloride - ether). IR: $\nu_{max}^{CHCl_3}$ cm$^{-1}$: 1744, 1729, 1607, 1559, 1496, 1250. UV: $\lambda_{max}^{EtOH}$ mμ (ε): 315 (29900; shoulder), 328 (39200), 343 (30600). NMR: ppm (CDCl$_3$): 1.10 (singlet, 3H, 13-Me), 2.10 (singlet, 3H, OCOMe), 3.79 (singlet, 3H, OMe), 5.06 (quartet, 1H, J = 5.0 and 10.5, 17aα-H), 6.06 (broad singlet, 1H, 15-H), 6.68 - 7.30 (multiplet, 3H, aromatic protons). Anal. Calcd. for C$_{21}$H$_{24}$O$_3$S (%): C, 70.75; H, 6.79; S, 9.00. Found (%): C, 70.57; H, 6.81; S, 9.12.

The following compounds can be prepared in the same manner as mentioned above.

3-Methoxy-18-methyl-16-thia-D-homo-1,3,5(10),8,14-estrapentaen-17aα-ol (Ib: $R^1 = Et; R^2 = Me; R^5 = H; X = S$): mp. 112.5°–114° C. (recrystallized from ether - pentane). IR: $\nu_{max}^{CHCl_3}$ cm$^{-1}$: 1607, 1561, 1494; $\nu_{max}^{CCl_4}$ cm$^{-1}$: 3554. UV: $\lambda_{max}^{EtOH}$ mμ (ε): 316 (27000; shoulder), 330 (36500), 345 (28000). Anal. Calcd. for C$_{20}$H$_{24}$O$_2$S (%): C, 73.13; H, 7.37; S, 9.76. Found (%): C, 72.91; H, 7.34; S, 9.79.

3-Methoxy-18-methyl-16-thia-D-homo-1,3,5(10),8,14-estrapentaen-17aα-ol (Ib: $R^1 = Et; R^2 = Me; R^5 = H; X = S$): mp. 100°–101.5° C. (recrystallized from ether - pentane). IR: $\nu_{max}^{CHCl_3}$ cm$^{-1}$: 1607, 1563, 1494; $\nu_{max}^{CCl_4}$ cm$^{-1}$: 3631. UV: $\lambda_{max}^{EtOH}$ mμ (ε): 315 (27700; shoulder), 329.5 (37500), 344 (27900). NMR: ppm (CDCl$_3$): 0.96 (triplet, 3H, J = 7.0, 18-Me), 3.79 (singlet, 3H, OMe), 6.06 (singlet, 1H, 15-H), 6.66 - 7.29 (multiplet, 3H, aromatic protons). Anal. Calcd. for C$_{20}$H$_{24}$O$_2$S (%): C.73.13; H. 7.37; S, 9.76. Found (%): C, 72.88; H, 7.35; S, 10.01.

3-Methoxy-16-oxa-D-homo-1,3,5(10),8,14-estrapentaen-17aα-ol (Ib: $R^1 = R^2 = Me; R^5 = H; X = O$): mp.

140.5°-142° C. (recrystallized from methylene chloride - ether). IR: $\nu_{max}^{CHCl_3}$ cm$^{-1}$: 1618, 1563, 1493; $\nu_{max}^{CCl_4}$ cm$^{-1}$: 3633, 3613 (shoulder). UV: $\lambda_{max}^{EtOH}$ mμ (ε): 299 (23000; shoulder), 311 (27900), 323 (21300; shoulder). Anal. Calcd. for C$_{19}$H$_{22}$O$_3$(%): C, 76.48; H, 7.43. Found (%): C, 76.27; H, 7.45.

17aβ-Acetoxy-3-methoxy-16-oxa-D-homo-1,3,5(10),8,14-estrapentaene (Ib: R$^1$ = R$^2$ = Me; R$^5$ = Ac; X = O): mp. 161°-164° C. (recrystallized from methylene chloride - ether). IR: $\nu_{max}^{CHCl_3}$ cm$^{-1}$: 1736, 1620, 1563, 1493, 1243. NMR: ppm (CDCl$_3$): 1.13 (singlet, 3H, 13-Me), 2.11 (singlet, 3H, OCOMe), 3.79 (singlet, 3H, OMe), 5.00 (quartet, 1H, J = 5 and 10, 17aα-H), 6.58 (broad singlet, 1H, 15-H), 6.67 - 7.27 (multiplet, 3H, aromatic protons).

3-Methoxy-18-methyl-16-oxa-D-homo-1,3,5(10),8,14-estrapentaen-17aα-ol (Ib: R$^1$ = Et; R$^2$ = Me; R$^5$ = H; X = O): mp. 105.5°-107° C. (recrystallized from ether - pentane). IR: $\nu_{max}^{CHCl_3}$ cm$^{-1}$: 1620, 1564, 1495; $\nu_{max}^{Cll_4}$cm$^{-1}$: 3632. UV: $\lambda_{max}^{EtOH}$ mμ (ε): 300 (23700; shoulder), 312.2 (28300), 324 (21500; shoulder). NMR: ppm (CDCl$_3$): 0.94 (triplet, 3H, J = 7.5, 18-Me), 3.79 (singlet, 3H, OMe), 6.61 (broad singlet, 1H, 15-H), 6.65 - 7.24 (multiplet, 3H, aromatic protons). Anal. Calcd. for C$_{20}$H$_{24}$O$_3$ (%): C, 76.89; H, 7.74. Found (%): C, 76.67; H, 7.83.

16-Thia-D-homo-1,3,5(10),8,14-estrapentaene-3,17aβ-diol (Ib: R$^1$ = Me; R$^2$ = R$^5$ = H; X = S)

Ethanethiol (625 mg; 10 mmole), dissolved in 10 ml of dry dimethylformamide, is added to a suspension of 500 mg (10.5 mmole) of 50% sodium hydride in mineral oil in 5 ml of dry dimethylformamide under nitrogen, and the mixture is stirred for 5 minutes. A solution of 500 mg (1.59 mmole) of 3-methoxy-16-thia-D-homo-1,3,5(10),8,14-estrapentaen-17aα-ol in 5 ml of dry dimethylformamide is added therein, and the solution is refluxed for 1.5 hours. The cooled mixture is acidified with an aqueous hydrochloric acid solution and extracted with chloroform - methanol (9:1). The organic layer is washed with an aqueous sodium chloride solution, dried over anhydrous sodium sulfate and evaporated in vacuo. Trituration with methylene chloride gives 417.9 mg of the 3-ol as crystalline solid, mp. 224°-227° C.

The mother liquor residue is purified by passing through a short column of silica gel and eluating with petroleum ether - benzene and then with methylene chloride to give 8.1 mg of an additional crop, mp. 220°-225° C. Total yield is 426.0 mg (89.2%). Recrystallization from methylene chloride gives the analytical specimen, mp. 231°-234° C. IR: $\nu_{max}^{KBr}$ cm$^{-1}$: 3427, 3312, 1604, 1572, 1552, 1499. UV: $\lambda_{max}^{EtOH}$ mμ (ε): 315 (33900; shoulder), 328.5 (44200), 343 (33600). NMR: ppm (d$_6$-DMSO): 0.92 (singlet, 3H, 13-Me), 5.12 (multiplet, 1H, J = 10, 17aα-H), 6.10 (broad singlet, 1H, 15-H), 6.54 - 7.20 (multiplet, 3H, aromatic protons). Anal. Calcd. for C$_{18}$H$_{20}$O$_2$S(%): C, 71.96; H, 6.71; S, 10.67. Found (%): C, 71.78; H, 6.63; S, 10.33.

The following compound can be prepared in the same manner as mentioned above.

16-Thia-D-homo-1,3,5(10),8,14-estrapentaene-3,17aα-diol (Ib: R$^1$ = Me; R$^2$ = R$^5$ = H; X = S): mp. 197-198.5° C. (recrystallized from methanol - methylene chloride). IR: $\nu_{max}^{KBr}$ cm$^{-1}$: 3406, 3236, 1608, 1601, 1566, 1498. UV: $\lambda_{max}^{EtOH}$ mμ (ε): 317 (28200; shoulder), 329 (36900), 345 (27800),; NMR: ppm (d$_6$-DMSO): 0.88 (singlet, 3H, 13-Me), 4.66 (broad doublet, 1H, J = 5.0, 17aβ-H), 6.16 (broad singlet, 1H, 15-H), 6.53 - 7.18 (multiplet, 3H, aromatic protons). Anal. Calcd. for C$_{18}$H$_{20}$O$_2$S (%): C, 71.96; H, 6.71; S, 10.67. Found (%): C, 71.68; H, 6.74; S, 10.47.

EXAMPLE 3

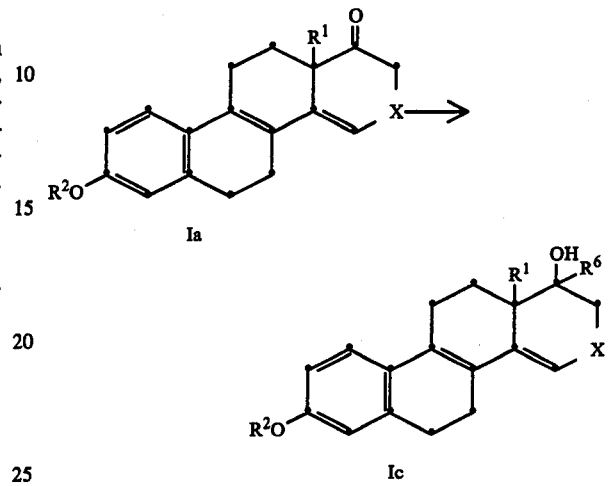

3-Methoxy-17a-methyl-16-thia-D-homo-1,3,5(10),8,14-estrapentaen-17a-ols (Ic: R$^1$ = R$^2$ = R$^6$ = Me; X = S)

A Grignard reagent (MeMgI) is prepared from 7.45 g (52.5 mmole) of methyl iodide, 1.24 g (51.2 mg atom) of magnesium and a total of 40 ml of dry ether. To the ice-cold Grignard solution is slowly added with stirring a solution of 2.0 g (6.4 mmole) of 3-methoxy-16-thia-D-homo-1,3,5(10),8,14-estrapentaen-17a-one in 40 ml of dry tetrahydrofuran, and the mixture is stirred at room temperature for 7 hours. The mixture is then cooled and hydrolyzed with an ice-cold solution of ammonium chloride, the organic layer is separated, and the aqueous layer is extracted with ether - methylene chloride (3:1). The organic layers are combined, washed with an aqueous sodium chloride solution, dried over anhydrous sodium sulfate, and evaporated in vacuo. The crude product is checked by thin layer chromatography, which shows approximately half of the starting material still remaining unchanged. Thus, the crude product is repeatedly treated with an additional 25.6 mmole of methyl magnesium iodide and worked up in the same manner as mentioned above. The finally resultant residue is purified by preparative thin layer chromatography using silica gel and benzene-ethyl acetate (9:1).

The upper band gives 867 mg (43.3% yield) of the starting material.

The middle band gives 599 mg (50.3% yield) of the 17aα-ol (Ic: R$^1$ = R$^2$ = Me; R$^6$ = β-Me; X = S), which is crystallized from ether to give 565.2 mg of crystals, mp. 183°-184° C. Recrystallization from methylene chloride - ether gives the pure analytical specimen, mp. 183.5°-184.5° C. IR: $\nu_{max}^{CHCl_3}$ cm$^{-1}$: 1607, 1561, 1492; $\nu_{max}^{CCl_4}$cm$^{-1}$: 3554. UV: $\lambda_{max}^{EtOH}$ mμ (ε): 316 (27700; shoulder), 330 (36500), 344 (27800; shoulder). NMR: ppm (CDCl$_3$): 1.04 (singlet, 3H, 13-Me), 1.36 (singlet, 3H, 17aβ-Me), 3.78 (singlet, 3H, OMe), 6.19 (broad singlet, 1H, 15-H), 6.66 - 7.29 (multiplet, 3H, aromatic protons). Anal. Calcd. for C$_{20}$H$_{24}$O$_2$S (%): C, 73.13; H, 7.37; S, 9.76. Found (%): C, 72.84; H, 7.35; S, 9.66.

The lower band gives 416.9 mg (35.0% yield) of the 17aβ-ol (Ic: R$^1$ = R$^2$ = Me; R$^6$ = α-Me; X = S), which is crystallized from ether - pentane to give 357.1 mg of crystals, mp. 152°-156° C. Recrystallization from methylene chloride - ether gives the analytical specimen, mp. 153°-155° C. IR: $\nu_{max}^{CHCl_3}$ cm$^{-1}$: 1608, 1560, 1492; $\nu_{max}^{CCl_4}$ cm$^{-1}$: 3618. UV: $\lambda_{max}^{EtOH}$ mμ (ε): 316 (24500; shoulder), 330 (32900), 345 (25500). NMR: ppm (CDCl$_3$): 1.08 (singlet, 3H, 13-Me), 1.40 (singlet, 3H, 17aα-Me), 3.78 (singlet, 3H, OMe), 6.02 (broad singlet, 1H, 15-H), 6.66 - 7.29 (multiplet, 3H, aromatic protons). Anal. Calcd. for C$_{20}$H$_{24}$O$_2$S (%): C, 73.13; H, 7.37; S, 9.76. Found (%): C, 72.89; H, 7.36; S, 10.03.

17a-Ethynyl-3-methoxy-16-thia-D-homo-1,3,5(10),8,14-estrapentaen-17a-ols (Ic: R$^1$ = R$^2$ = Me; R$^6$ = C≡CH; X = S)

A solution of 2.0 g (6.4 mmole) of 3-methoxy-16-thia-D-homo-1,3,5(10),8,14-estrapentaen-17a-one in 130 ml of dry tetrahydrofuran and a solution of 2.0 g of potassium in 30 ml of dry t-amyl alcohol are added with stirring to 130 ml of dry tetrahydrofuran saturated with purified acetylene gas over a period of about 1 hour. Stirring is continued at room temperature for 6 hours with continuous bubbling of acetylene. Finally, the reaction mixture saturated with acetylene is kept at 0° C. in a refrigerator overnight and then decomposed with an aqueous ammonium chloride solution. Extraction with ether - methylene chloride (3:1) followed by usual work-up gives the crude product (1.89 g), which is purified by preparative thin layer chromatography using silica gel and benzene-ethyl acetate (20:1).

The upper band gives 1.296 g (59.8% yield) of the 17aα-ol, (Ic: R$^1$ = R$^2$ = Me; R$^6$ = 17aβ-C≡CH; X = S), which is crystallized from methylene chloride - ether to give 1.26 g of crystalline product, mp. 173.5°-174° C. IR: $\nu_{max}^{Nujol}$ cm$^{-1}$: 2100, 1608, 1597, 1561, 1496; $\nu_{max}^{CCl_4}$ cm$^{-1}$: 3540. UV: $\mu_{max}^{EtOH}$ mμ (ε): 316 (28200; shoulder), 329.5 (37700), 345 (28800). NMR: ppm (C$_5$D$_5$N): 1.30 (singlet, 3H, 13-Me), 3.40 (singlet, 1H, C≡CH), 3.73 (singlet, 3H, OMe), 6.40 (broad singlet, 1H, 15-H). Anal. Calcd. for C$_{21}$H$_{22}$O$_2$S (%): C, 74.52; H, 6.55; S, 9.47. Found (%): C, 74.28; H, 6.47; S, 9.22.

The lower band gives 0.108 g (5.0%) of the 17aβ-ol, which is crystallized from tetrahydrofuran - ether to give 84.9 mg of a crystalline product, mp. 214°-216° C. IR: $\nu_{max}^{Nujol}$ cm$^{-1}$: 2100, 1603, 1595, 1495, 1552; $\nu_{max}^{CCl_4}$ cm$^{-1}$: 3612. UV: $\lambda_{max}^{EtOH}$ mμ (ε): 316 (28400; shoulder), 329.5 (38200), 345 (29400). NMR: ppm (C$_5$D$_5$N): 1.33 (singlet, 3H, 13-Me), 3.23 (singlet, 1H, C≡CH), 3.73 (singlet, 3H, OMe), 6.37 (broad singlet, 1H, 15-H). Anal. Calcd. for C$_{21}$H$_{22}$O$_2$S (%): C, 74.52; H, 6.55; S, 9.47. Found (%): C, 74.21; H, 6.53; S, 9.29.

17a-Benzyl-3-methoxy-16-thia-D-homo-1,3,5(10),8,14-estrapentaen-17a-ols (Ic: R$^1$ = R$^2$ = Me; R$^6$ = CH$_2$Ph; X = S)

To an ice-cold Grignard reagent preliminarily prepared from 9.21 g (53.9 mmole) of benzyl bromide, 1.26 g (51.9 mg atom) of magnesium, 15 ml of dry ether and 10 ml of dry tetrahydrofuran is dropwise added with stirring a solution of 2.08 g (6.66 mmole) of 3-methoxy-16-thia-D-homo-1,3,5(10),8,14-estrapentaen-17a-one in 15 ml of dry tetrahydrofuran. The mixture is stirred at room temperature for 13 hours and then refluxed for 7 hours followed by standing overnight. Usual work-up gives an oily residue (8.8 g), which contains a large amount of a non-polar compound to be presumed as 1,2-diphenylmethane. This is spearated by passing through a column of 30 g of neutral alumina and eluating with petroleum ether, petroleum ether - benzene (9:1), petroleum ether- benzene (1:1), benzene, benzene - methylene chloride (1:1), and methylene chloride, successively.

The fractions of from petroleum ether to benzene - methylene chloride (1:1) are further separated by thin layer chromatography (silica gel; benzene-n-hexane (1:1)). The upper band gives 450.8 mg (21.7%) of the starting ketone, the middle band 346.1 mg of the 17aα-ol, and the lower band 42.5 mg of the 17aβ-ol.

Thin layer chromatography (silica gel; benzene) of the above methylene chloride fraction gives an additional 287 mg of the 17aα-ol and 278.7 mg of the 17aβ-ol. Total yields of the 17aα-ol and the 17aβ-ol were 633.1 mg (30.1%) and 321.2 mg (15.2%) respectively.

These compounds have the following physical properties.

The 17aα-ol (Ic: R$^1$ = R$^2$ = Me; R$^6$ = β-CH$_2$Ph; X = S): mp. 155°-157° C. (recrystallized from carbon tetrachloride - ether). IR: $\nu_{max}^{CHCl_3}$ cm$^{-1}$: 1606, 1561, 1493; $\nu_{max}^{CCl_4}$ cm$^{-1}$: 3553. UV: $\lambda_{max}^{EtOH}$ mμ (ε): 316 (26700; shoulder), 330 (35300), 345 (27000; shoulder). NMR: ppm (CDCl$_3$): 1.14 (singlet, 3H, 13-Me), 3.79 (singlet, 3H, OMe), 6.20 (broad singlet, 1H, 15-H), 6.67-7.30 (multiplet, 8H, aromatic protons). Anal. Calcd. for C$_{26}$H$_{28}$O$_2$S (%): C, 77.19; H, 6.98; S, 7.93. Found (%): C, 77.08; H, 6.91; S, 7.74.

The 17aβ-ol (Ic: R$^1$ = R$^2$ = Me; R$^6$ = α-CH$_2$PH; X = S): mp. 143°-144.5° C. (recrystallized from carbon tetrachloride - ether). IR: $\nu_{max}^{CHCl_3}$ cm$^{-1}$: 1608, 1561, 1494; $\nu_{max}^{CCl_4}$ cm$^{-1}$: 3611, 3580. UV: $\lambda_{max}^{EtOH}$ mμ (ε): 317 (27400; shoulder), 331 (37800), 346.5 (28900). NMR: ppm (CDCl$_3$): 1.15 (singlet, 3H, 13-Me), 3.78 (singlet, 3H, OMe), 6.13 (broad singlet, 1H, 15-H), 6.67-7.50 (multiplet, 8H, aromatic protons). Anal. Calcd. for C$_{26}$H$_{28}$O$_2$S (%): C, 77.19; H, 6.98; S, 7.93. Found (%): C, 76.93; H, 6.93; S, 7.80.

EXAMPLE 4

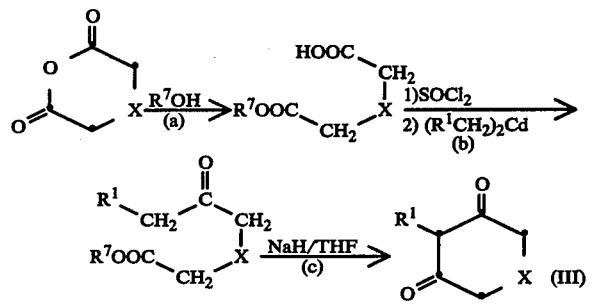

The starting diglycolic anhydride and thiodiacetic anhydride may be prepared from commercially available diglycolic acid and thiodiacetic acid [H. L. Morrill et al., J. Org. Chem., 26, 4103 (1961)]

(a) Methyl 2-(chloroformylmethylmercapto)acetate

A mixture of 82.2 g (0.63 mole) of thiodiacetic anhydride and 20.2 g (0.63 mole) of methanol is heated at 60°-70° C. under stirring for 1 hour. To the resulting homogeneous liquid, 91 ml (1.25 mole) of thionyl chloride is added dropwise while hydrogen chloride and sulfur dioxide evolved are continuously trapped through an aqueous sodium hydroxide solution. The solution is allowed to stand at room temperature overnight until no gas evolved. The excess amount of thionyl chloride is removed under reduced pressure and the residual liquid is fractionally distilled to give 105.8 g (94.2% yield) of the acid chloride, bp. 129°-130° C./17 mmHg. This is purified by redistillation to give 99.0 g (86.5% yield) of the pure material, bp. 125°-126° C./13 mmHg. IR: $\nu_{max}^{Neat}$ cm$^{-1}$: 1800, 1740; $\nu_{max}^{CHCl_3}$ cm$^{-1}$: 1797, 1742. NMR: ppm (CDCl$_3$): 3.38 (singlet, 2H, CH$_2$COO), 3.75 (singlet, 3H, COOMe), 3.93 (singlet, 2H, CH$_2$COCl). Anal. Calcd. for C$_5$H$_7$O$_3$SCl (%): C, 32.88; H, 3.86; S, 17.56. Found (%): C, 32.68; H, 3.88; S, 17.40.

(b) Methyl 2-(3-methylacetonylmercapto)acetate

To a stirred ice-cold ethereal Grignard solution (392 ml) containing 0.56 mole of ethylmagnesium bromide, is added 51.3 g (0.28 mole) of dry powdered cadmium chloride in small portions. Stirring is continued without heating for 5 minutes, followed by refluxing for 30–45 minutes until no Gilman test for Grignard reagent is observed. Then, 500 ml of dry benzene is added thereto, and the resulting cadmium reagent is cooled to below 0° C. (usually −10° to 0° C.). A solution of 91.3 g (0.5 mole) of methyl 2-(chloroformylmethylmercapto)acetate in 500 ml of dry benzene is added with vigorous stirring as rapidly as consistent with control of the exothermic reaction. The reaction mixture is stirred at room temperature for 3–5 hours, then decomposed by addition of cold 6N sulfuric acid, and extracted three times with ether. The organic extracts are combined, washed successively with an aqueous sodium bicarbonate solution and an aqueous sodium chloride solution and dried over sodium sulfate. After evaporation of the solvent in vacuo, the residual liquid is distilled under reduced pressure to give 53.7 g (60.9% yield) of methyl 2-(3-methylacetonylmercapto)acetate as an oily material, bp. 137°-140° C./13 mmHg). IR: $\nu_{max}^{Neat}$ cm$^{-1}$: 1740, 1711; $\nu_{max}^{CHCl_3}$ cm$^{-1}$: 1737, 1712. NMR: ppm (CDCl$_3$): 1.10 (triplet, 3H, J = 7, CH$_2$CH$_3$), 2.62 (quartet, 2H, J = 7, CH$_2$CH$_3$), 3.28 (singlet, 2H, SCH$_2$COO), 3.43 (singlet, 2H, SCH$_2$CO), 3.73 (singlet, 3H, COOMe). Anal. Calcd. for C$_7$H$_{12}$O$_3$S (%): C, 47.70; H, 6.86; S, 18.19. Found (%): C, 47.96; H, 6.98; S, 17.90.

(c) 4-Methyltetrahydrothiopyran-3,5-dione (III: R$^1$ = Me; X = S)

A solution of 101.3 g (0.57 mole) of methyl 2-(3-methylacetonylmercapto)acetate in 2.3 liter of dry tetrahydrofuran is added dropwise over a period of 3 hours to a stirred suspension of 0.57 mole of sodium hydride (27.4 g of 50% mineral oil suspension) in 1.1 liter of dry tetrahydrofuran at room temperature under nitrogen. Stirring is continued for an additional 3 hours. The resulting yellow reaction mixture is concentrated to a small volume at temperature below 40° C. under reduced pressure, poured into ice-cold water and then extracted with ether. The aqueous layer is acidified at pH 2-3 with dilute hydrochloric acid and extracted several times with chloroform. The extracts are washed with a small portion of an aqueous sodium chloride solution and dried over anhydrous sodium sulfate. The solvent is removed in vacuo and the residue is crystallized from methylene chloride - ether to give 62.7 g (75.6% yield) of 4-methyltetrahydrothiopyran-3,5-dione, mp. 131°-133° C. Recrystallization from acetone - ether gives an analytical specimen, mp. 132.5°-133° C. IR: $\nu_{max}^{CHCl_3}$ cm$^{-1}$: 1735, 1705, 1631; $\nu_{max}^{Nujol}$ cm$^{-1}$:1635, 1553. UV: $\lambda_{max}^{95\%EtOH}$ mμ (ε): 275 (9500), 315 (2400); $\lambda_{max}^{N-HCl}$ mμ (ε): 272 (9900); $\lambda_{max}^{N-NaOH}$ mμ (ε): 289 (11600), 316 (12900). NMR: ppm (CDCl$_3$): 1.28 (doublet, 3H, J = 7, Me), 3.44 (singlet, 4H, 2-H$_2$ and 6-H$_2$), 3.73 (quartet, 1H, J = 7, 4-H); ppm (CD$_3$OD): 1.69 (broad singlet, 3H, vinyl-Me), 3.34 (broad singlet, 4H, 2-H$_2$ and 6-H$_2$). Anal. Calcd. for C$_6$H$_8$O$_2$S (%): C, 49.98; H, 5.59; S, 22.24. Found (%): C, 50.17; H, 5.50; S, 22.14.

The following compounds can be prepared in the same manner as mentioned above.

4-Ethyltetrahydrothiopyran-3,5-dione (III: R$^1$ = Et; X = S): mp. 108.5°-109.5° C. (recrystallized from methylene chloride - ether). IR: $\nu_{max}^{CHCl_3}$ cm$^{-1}$: 1736, 1703, 1623; $\nu_{max}^{Nujol}$ cm$^{-1}$: 1570. UV: $\lambda_{max}^{95\%EtOH}$ mμ (ε): 273 (9600), 317 (1200). NMR: ppm (CDCl$_3$): 0.95 (triplet, 3H, J = 7.5, Me), 1.93 (quintet, 2H, J = 7.5, CH$_2$CH$_3$), 3.41 (singlet, 4H, 2-H$_2$ and 6-H$_2$); ppm (CD$_3$OD): 0.92 (triplet, 3H, J = 7.5 Me), 1.84 (broad quartet, 0.42H, J = 7.5, CH$_2$CH$_3$), 2.32 (quartet, 1.58H, J = 7.5, vinyl CH$_2$CH$_3$), 3.34 (singlet, 4H, 2-H$_2$ and 6-H$_2$). Anal. Calcd. for C$_7$H$_{10}$O$_2$S (%): C, 53.14; H, 6.27; S, 20.27. Found (%): C, 53.07; H, 6.35; S, 20.18.

4-Methyltetrahydropyran-3,5-dione (III: R$^1$ = Me; X = O): mp. 178°-180° C. (recrystallized from chloroform containing a small amount of methanol). IR: $\nu_{max}^{CHCl_3}$ cm$^{-1}$: 1755, 1725, 1642; $\nu_{max}^{Nujol}$ cm$^{-1}$: 1653, 1570. UV: $\lambda_{max}^{95\%EtOH}$ mμ (ε): 261.5 (15700), 291 (4000; shoulder). NMR: ppm (CDCl$_3$ - CD$_3$OH = 98:2): 1.26 (doublet, 0.825H, J = 7, Me), 1.74 (broad singlet, 2.175H, vinyl Me), 4.21 (broad singlet, 4H, 2-H$_2$ and 6-H$_2$); ppm (CD$_3$OD): 1.70 (broad singlet, 3H, vinyl Me), 4.18 (broad singlet, 4H, 2-H$_2$ and 6-H$_2$). Anal. Calcd. for C$_6$H$_8$O$_3$ (%): C, 56.24; H, 6.29. Found (%): C, 56.36; H, 6.37.

4-Ethyltetrahydropyran-3,5-dione (III: R$^1$ = Et; X = O): mp. 117°-119° C. (recrystallized from methylene chloride - ether). IR: $\nu_{max}^{CHCl_3}$ cm$^{-1}$: 1756, 1721, 1626; $\nu_{max}^{Nujol}$ cm$^{-1}$: 1617 (shoulder), 1570. UV: $\lambda_{max}^{95\%EtOH}$ Mμ (ε): 261.5 (12200). NMR: ppm (CDCl$_3$): 1.01 (triplet, 3H, J = 8, Me), 1.85 (quintet, 0.28H, J = 7-8, CH$_2$CH$_3$), 2.35 (quartet, 1.72H, J = 8, vinyl CH$_2$), 4.27 (singlet, 4H, 2-H$_2$ and 6-H$_2$). Anal. Calcd. for C$_7$H$_{10}$O$_3$ (%): C, 59.14; H, 7.09. Found (%): C, 58.80; H, 7.03.

We claim:
1. A compound of the formula

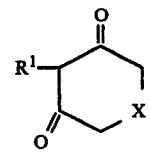

wherein R$^1$ represents lower alkyl of 1 to 5 carbon atoms and X represents oxygen or sulfur.

2. A compound according to claim 1 wherein X is sulfur and R$^1$ is methyl.

3. A compound according to claim 1 wherein X is sulfur and R$^1$ is ethyl.

4. A compound according to claim 1 wherein X is oxygen and R$^1$ is methyl.

5. A compound according to claim 1 wherein X is oxygen and R$^1$ is ethyl.

* * * * *